United States Patent [19]

Loeser

[11] Patent Number: 5,403,346
[45] Date of Patent: Apr. 4, 1995

[54] SELF-AFFIXING SUTURE ASSEMBLY

[76] Inventor: Edward A. Loeser, 8646 Oak Valley Dr., Sandy, Utah 84093-2015

[21] Appl. No.: 998,950

[22] Filed: Dec. 31, 1992

[51] Int. Cl.$^6$ ............................................. A61L 17/00
[52] U.S. Cl. ..................................................... 606/228
[58] Field of Search ................ 606/151, 157, 191, 213, 606/215, 216, 218, 228, 232; 24/16 PB

[56] References Cited

U.S. PATENT DOCUMENTS

| | | |
|---|---|---|
| 2,764,159 | 9/1956 | Masci et al. |
| 3,123,077 | 3/1964 | Alcamo |
| 3,225,766 | 12/1965 | Baptist et al. |
| 3,463,158 | 8/1969 | Schmitt et al. |
| 3,527,841 | 9/1970 | Wicker, Jr. et al. |
| 3,564,078 | 2/1971 | Wicker, Jr. et al. |
| 3,570,497 | 3/1971 | Lemole |
| 3,577,601 | 5/1971 | Mariani et al. ............ 606/151 |
| 3,636,956 | 1/1972 | Schneider |
| 3,739,773 | 6/1973 | Schmitt et al. |
| 3,759,264 | 9/1973 | Coover, Jr. et al. |
| 3,772,420 | 11/1973 | Glick et al. |
| 3,883,901 | 5/1975 | Coquard et al. |
| 4,271,838 | 6/1981 | Lasner et al. |
| 4,548,202 | 10/1985 | Duncan |
| 4,693,246 | 9/1987 | Reimels |
| 4,730,615 | 3/1988 | Sutherland et al. ......... 606/215 |
| 4,773,421 | 9/1988 | Davis |
| 4,836,205 | 6/1989 | Barrett |
| 4,890,615 | 1/1990 | Caspari et al. |
| 4,901,721 | 2/1990 | Hakki |
| 4,901,722 | 2/1990 | Noguchi |
| 4,932,962 | 6/1990 | Yoon et al. |
| 4,935,027 | 6/1990 | Yoon |
| 4,950,284 | 8/1990 | Green et al. ............... 606/151 |
| 4,950,285 | 8/1990 | Wilk ......................... 606/232 |
| 4,957,498 | 9/1990 | Caspari et al. |
| 4,961,741 | 10/1990 | Hayhurst |
| 4,981,149 | 1/1991 | Yoon et al. |
| 5,015,250 | 5/1991 | Foster |
| 5,053,047 | 10/1991 | Yoon |
| 5,074,874 | 12/1991 | Yoon et al. |
| 5,084,058 | 1/1992 | Li |
| 5,100,418 | 3/1992 | Yoon et al. |
| 5,102,421 | 4/1992 | Anspach, Jr. |

OTHER PUBLICATIONS

Novak's Textbook of Gynecology, "Chapter 1, History, Examination and Operation", pp. 26–27.
XIV. Family Planning, "Chapter 62, Surgical Contraception", pp. 1353–1357.

*Primary Examiner*—Tamara L. Graysay
*Attorney, Agent, or Firm*—Trask, Britt & Rossa

[57] ABSTRACT

Disclosed is an elongate suture having a longitudinal axis, a needle end, a latch collar end, and a node for interacting with the latch collar end. The node lays laterally on the elongate suture transverse to the longitudinal axis and has a proximal and a distal edge with respect to the needle end. In the invention, a portion of the node's proximal edge is perpendicular to the elongate suture's longitudinal axis thus acting to prevent forward movement after the suture has been placed. Between the proximal and distal edges of a single notch is a top surface. This top surface will usually be planar or convex. In one embodiment of the device, the elongate suture has multiple nodes. The nodes are then spacedly positioned along the longitudinal axis of the suture cord, thus forming notches between the nodes. These notches are sized in relation to the collar to allow it to move along the longitudinal surface when the stitched tissue moves.

7 Claims, 3 Drawing Sheets

SELF-AFFIXING SUTURE ASSEMBLY

TECHNICAL FIELD

The invention relates to a suture device useful in surgery in general, and to a self-affixing suture assembly in particular.

BACKGROUND

U.S. Pat. No. 3,570,497 to Lemole (Mar. 16, 1971) discloses a suture apparatus having a needle end, cord of latch notches, and a latch collar end. To use the suture, a needle is first affixed to the needle end. A surgeon then pulls the needle through the tissue to be sewn and the needle, followed by the cord for a number of latch notches selected by the surgeon, is continued on through the collar latch passage. The surgeon then severs the suture above the last notch pulled through the latch collar to complete a stitch. U.S. Pat. No. 5,053,047 to Yoon (Oct. 1, 1991) discloses somewhat similar suture devices (see, e.g. FIGS. 4 through 9 of the Yoon patent). The devices are asserted to be useful as suture devices since they can cinch tissue without the need to tie a knot in the suture cord.

One drawback of these devices however is that, due to the way they are designed, they can continue closing thus further constricting the tissue even after the surgeon has "completed" the cinching process. This can especially occur when the stitched tissue moves. Due to movement of the stitched tissue, the needle end of the suture cord can be continually pushed through the collar thus tightening the device. Since the cord has latches, movement in the opposite "loosening" direction is prevented. If the needle end is pushed far enough in the tightening direction however, the next "latch notch" will interact with the collar, and the suture will tighten further possibly causing pain and tissue damage.

These devices also, when they are cinched, do not allow for much movement or "play" in the suture near the connection point thus possibly damaging the stitched tissue more than absolutely necessary when the stitched tissue moves.

DISCLOSURE OF THE INVENTION

The invention includes a suture which includes an elongate base structure having a needle end, a collar end, and at least one node for interacting with the collar end. The node is positioned on the elongate base structure transverse to the base structure's longitudinal axis, and has a proximal and a distal edge with respect to the needle end (a "leading" and "trailing" edge, respectively). In the invention, a portion of the node's proximal edge is perpendicular to the elongate base structure's longitudinal axis thus acting to prevent further cinching of the device once it has been finally placed. The distal edge of the node may also be wholly or partially perpendicular to the elongate base structure's longitudinal axis.

Between the proximal and distal edges of a single notch is a top surface. This top surface will usually be planar or convex. A planar top surface can be, but need not be, parallel to the base structure's longitudinal axis.

In one embodiment of the device, the elongate suture has multiple nodes. The nodes will then generally be positioned in a spaced relationship along the longitudinal axis of the suture cord, thus forming planar notches between the nodes. These notches can be sized to allow the collar or other structure to move along the longitudinal surface to a very limited extent to give the suture some "play", thus preventing possible tissue damage when the stitched tissue moves (e.g. by cutting into the local tissue surrounding the stitches). In such a case, the planar notch will generally be parallel to the elongate suture's longitudinal axis.

The invention also includes a ligature having an elongate surface with evenly spaced lateral ribs traversing the surface and an aperture, collar or other means, associated with one end of the ligature, for impeding movement of the ligature in one direction through the aperture while still allowing movement in the direction opposite to the impeded direction. Between the lateral ribs are notches. The notches will, in cross-section, lay substantially parallel to the elongate surface's longitudinal axis. The aperture is sized to encase the notch while still allowing limited bi-directional longitudinal movement of the aperture in the area of the notch between the ribs.

The invention also includes methods of making and using such devices. The device is useful for various surgical procedures that typically require suturing, especially stitching of tissue which moves.

BRIEF DESCRIPTION OF THE FIGURES

In the drawings, which depict presently preferred embodiments of the invention and in which like reference numerals refer to like parts in different views.

BEST MODE OF THE INVENTION

Figure 1:
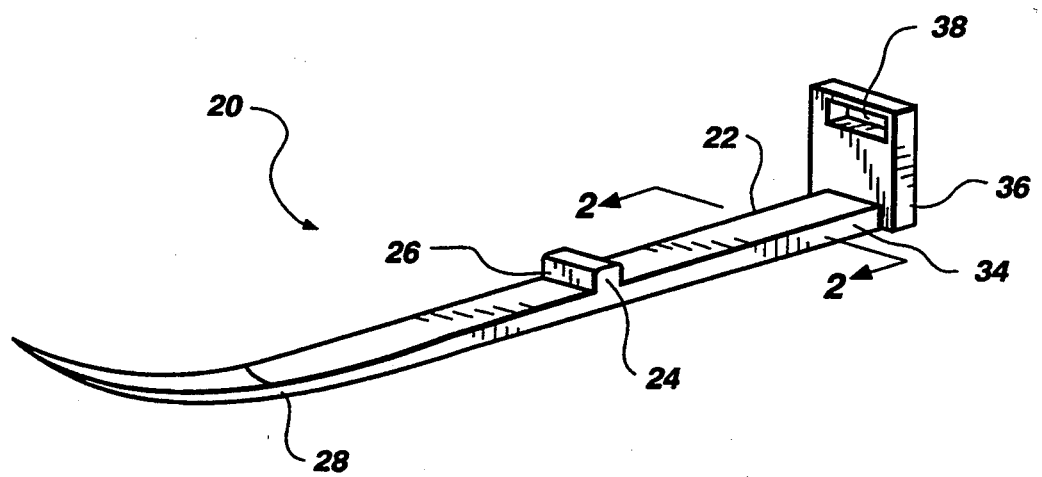
FIG. 1 is an enlarged isometric view of a suture device according to one embodiment of the invention.
Figure 2:
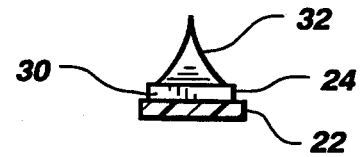
FIG. 2 is an enlarged cross-section taken along section lines 2—2 from FIG. 1.

As shown in FIG. 1, the suture, generally 20, has a base structure 22. This base structure 22 may be of various cross-sections, e.g. circular, rectangular, square, or elliptical, although a rectangular one is depicted (FIG. 2). The suture, generally 20, will typically vary in length from two to sixty centimeters, preferably from thirty to forty-five centimeters. The base structure will preferably have a width or diameter varying from 0.1 to three millimeters. In one preferred embodiment, the base structure has a uniform cross-sectional shape and dimension along its longitudinal axis.

The base structure is flexible enough to be stitched and is preferably made of a material strong enough to hold two pieces of tissue together after stitching. Acceptable materials for surgical sutures include those listed in the generalized monograph of the *United States Pharmacopeia*. These include absorbable and nonabsorbable sutures.

Examples of absorbable sutures include surgical gut ("catgut") and synthetic absorbable sutures such as thermoplastic polymers derived from condensing the cyclic derivative of glycolic acid (glycolide) and mixtures of glycolide and cyclicized lactic acid (lactide) (e.g. PLAGA). Materials and methods for making polyglycolic and polylactic are disclosed in U.S. Pat. Nos. 3,463,158; 3,739,773; 3,772,420; and 3,636,956, the contents of which are incorporated by this reference. Other absorbable polymers are disclosed in U.S. Pat. Nos. 3,225,766 and 3,883,901 (absorbable polyesters), U.S. Pat. No. 2,764,159 (absorbable cellulose glycolic acid ethers), and U.S. Pat. Nos. 3,527,841; 3,564,078; and 3,759,264 (esters of α-cyanoacrylic acid), the contents of all of which are incorporated by this reference. Examples of nonabsorbable sutures include silk, dermal silk sutures (e.g. coated with tanned gelatin), nylon, polyester fiber, polyolefin fibers, silver, and stainless steel. PLAGA fibers can be melt extruded.

Figure 3:
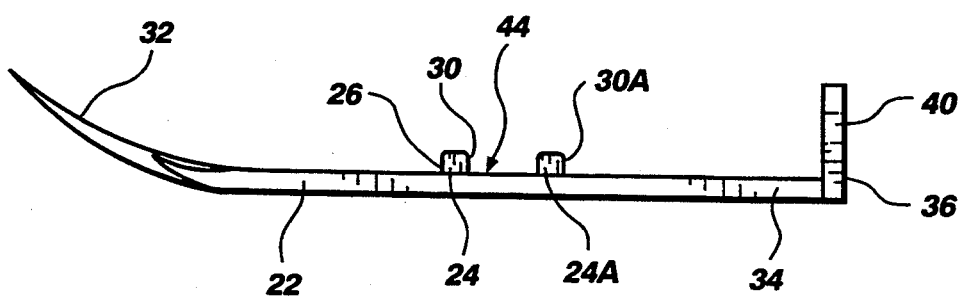
FIG. 3 is an enlarged side-view of a suture device according to one embodiment of the invention.

Positioned on the surface of the base structure 22 is a node 24 (or rib). This node 24 has an edge 26 proximate the needle end 28 of the suture. This proximal edge 26 sits perpendicular to the longitudinal axis of the base structure at the point of its association with the base structure (FIG. 3). It also has a distal edge 30 (with respect to the needle end 28 and any associated needle 32 (FIG. 2)). A rib or node may be integrally formed together with the base structure, or may be a separate piece affixed or attached to the base structure.

The diameter or cross-sectional area of the base structure with nodes will preferably be as close as possible to that of conventional ligature to prevent unnecessary tissue damage. In a preferred embodiment, the nodes add less than half a millimeter to the total diameter of the base structure.

On the end 34 of the base structure 22 distal to the needle 32 is a latch collar 36 or other structure for interacting with the node 24 or nodes 24, 24A (FIG. 3). The latch collar 36 or similar structure acts to prevent withdrawal of the needle 32 and base structure 22 once they have been inserted into the aperture 38. In order to prevent withdrawal of the base structure, a flange, hinged flexible flap or member, latch 40 or similar structure is preferably associated with the aperture 38. The height of the collar structure is typically chosen to adequately span the wound and accommodate the aperture. The use of a flap placed within the aperture or collar is especially preferred since it allows for relatively easy cinching of the device without the need for undue tension which might cause tissue damage during placement.

The latch collar 36 may be formed of the same material as the base structure. This is especially the case when the structure is intended to be absorbable. Alternatively the latch collar, or portions of it (e.g. the flap) may be formed of different materials if so desired. When the latch collar is made of the same material as the base structure, it can be integrally formed with the base structure.

FIG. 3 depicts another embodiment of the device having two nodes 24, 24A. Between the two nodes is a planar notch 44 having a length along the longitudinal axis of the base structure 22 at least that of the thickness of the latch collar 36. The length of the notch can be selected to provide very limited play of the collar about the notch (e.g. from 0.1 to one millimeter). In the embodiment depicted in FIG. 3, the nodes 24, 24A have a convex top surface to facilitate their entry and placement in the aperture 38, although planar, concave, and other shapes will also work.

In the embodiment depicted in FIGS. 1–3, the nodes or ribs are generally block-shaped and run perpendicular to the longitudinal axis of the suture. In cross-section, they will generally be square. The general block shape of such a rib is particularly advantageous when biodegradable suture material is used to form the ribbed suture. This advantage arises since during degradation of the suture material in the body, it will take some time for the ribs to erode sufficiently to allow the suture to back out of the latch collar end, thus preventing possible premature separation of the stitched tissues. In contrast with pointed nodes, the tip of the node can erode first, thus freeing, possibly prematurely, the latch collar to slide up the base structure and opening the wound.

Figure 4:
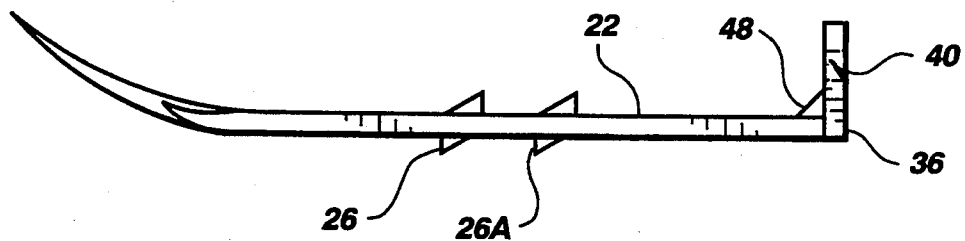
FIG. 4 is an enlarged side-view of a suture device according to one embodiment of the invention.
Figure 5:
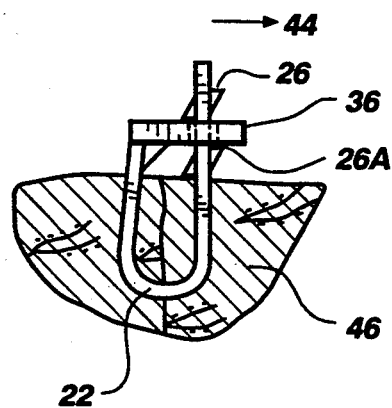
FIG. 5 is an enlarged elevational view of a stitch completed by the device of FIG. 4 with the needle removed.

FIG. 4 depicts another embodiment of the device. In this embodiment, the proximal edges 26, 26A are mounted on the opposite side of the base structure 22 than that shown in the previously described embodiments (FIGS. 1 to 3). This device also has at the base of the collar, a small thickening or other structure for abutment 48 against the tissue 46 once the suture has been placed (FIG. 5). This structure steadies the suture somewhat after placement.

In embodiments where the device has several nodes, the spacing between the distal edge of one node and the proximal edge of the next will typically vary from 0.1 to one millimeter thus forming several notches between the spaced ribs. Preferably the nodes will be evenly spaced.

In one embodiment, the notch portions between the evenly spaced ribs are pre-chosen allowing limited movement of the suture about the latch collar end. This movement gives the device some flexibility and decreases rigidity which can result in undue pain or tissue damage when the stitched tissue moves.

To use any of the depicted devices, the surgeon first prepares and orients the suture assembly to the extent necessary. The surgeon then pierces the tissue to be sutured with the needle 32 and draws it through the tissue (e.g. with forceps or a needle holder) with the flexible base structure 22 following up and cinching the wound. The needle 32 is then inserted into the aperture 38 which is sized and shaped to accept the base structure and accompanying node(s). In a device having multiple nodes 24, 24A the surgeon passes the collar end by an appropriate number of nodes to firmly cinch the tissue together. For a device such as that, this may require the surgeon to pull the base structure in a direction opposite to that of direction 44 (FIG. 5). The needle and appropriate amount of ligature is then cut off. The device, even though flexible, still tends to open, thus pushing the base structure in direction 44. Thus when tissue 46 moves, potentially driving the base structure further into the aperture 38, the proximal edge 26A butts up against the latch collar 36 preventing the device from further constricting the healing tissue 46.

Figure 6:
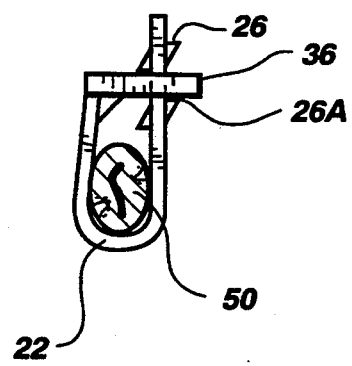
FIG. 6 is an enlarged view of a tubal ligation completed by a device according to the invention.

The device can be used for various surgical procedures. One especially useful procedure is a tubal ligation (FIG. 6). When a bioabsorbable material is used, the procedure is temporary, and may not require surgery to reopen the tubes 50. When the suture is not made of a bioabsorbable material, the device is especially useful for a Marshall-Marquette bladder suspension, bowel surgery, or for fastening a mesh during e.g. a hernia operation (see, e.g. U.S. Pat. No. 4,548,202 for a description of mesh having flexible filaments).

Various changes to the device can be made without departing from the spirit of the invention. For example in the case of a base structure having a circular cross-section, concentric ridges having a leading edge at least partially perpendicular to the longitudinal axis of the base structure, of preferably uniform height and dimension and evenly spaced from each other may extend around the surface of the base structure.

A kit according to the invention may contain an eyed needle together with several ligatures according to the invention. Alternatively, a kit according to the invention can contain several sutures to which respective needles have been attached together with a device for cutting off the needle and excess suture material (e.g. using a suture cutter such as that described in U.S. Pat. No. 4,271,838 to Lasner et al. (Jun. 9, 1981) at a point within the subject's body.

A needle for use with the invention is preferably an eyeless needle. An eyeless needle may be manufactured with an open channel into which the ribbed suture is placed, and the channel swaged around the suture. Alternatively, a "seamless" may be used, which has a very delicate hole drilled in the shank, and the shank is pressed firmly about the suture. In one embodiment, the eyeless needle can be removed from the strand by gently tugging on it. Needles such as those disclosed in U.S. Pat. No. 4,981,149 to Yoon et al. (Jan. 1, 1991) and U.S. Pat. No. 4,901,7222 to Noguchi (Feb. 20, 1990) may be used.

A preferred device for cutting off the needle and unused portion of the suture includes a barrel sized to accept the length of excess suture being used, associated with two separate sets of levers which, when actuated, provide the necessary mechanical action necessary to collect the needle and snip off the base structure of the suture.

At the end of the barrel of such a cutting device (distal to the user), there is an orifice or opening sized to receive a needle of the size being used. This distal end of the cutting device is inserted into a cavity in the subject and after the suture has been cinched, the needle is placed within the orifice. Actuating a first set of levers causes two rubber type geared wheels to rotate in opposite directions drawing the needle in and accepting it and the associated suture material into the barrel. A sufficient amount of suture material is of course left behind to provide sufficient tension for the stitched tissue to keep in apposition and heal.

Alternatively, the cutting device may employ a series of trapping flaps to enclose and contain the needle or needles and excess suture material. A second set of levers actuates two scissor blades just inside the orifice (and distal to the set of wheels) which cut the suture at the desired length, releasing the remaining portion of the suture. The procedure can be repeated, and the excess suture material and attached needles remain within the device until disposal occurs. When the device is full of needles and excess suture material or when the surgery is over, it is discarded.

Although the invention has been described with regard to certain preferred embodiments, the scope of the invention is defined by the appended claims.

What is claimed is:

1. A suture comprising:
   a flexible elongate base structure having a longitudinal axis, a needle end, and a second end;
   a collar for receiving a needle and affixed to said elongate base structure, positioned on said second end; and
   a plurality of nodes for interacting with the collar, said nodes positioned in spaced relationship along the longitudinal axis of said elongate base structure, between said needle and second ends, transverse to the longitudinal axis and each said node having a proximal and a distal edge with respect to the needle end of the flexible elongate base structure as well as a convex top surface extending between the proximal and distal edges, a portion of each said node's proximal edge relative said needle end being perpendicular to the elongate base structure's longitudinal axis, a planar notch existing between the proximal edge of a first of said nodes, and the distal edge of a second of said nodes.

2. The suture of claim 1 wherein said distal edge of each said node has a portion which is perpendicular to the elongate base structure's longitudinal axis.

3. The suture of claim 1 wherein said planar notch is parallel to the elongate base structure's longitudinal axis.

4. The suture of claim 1 further comprising means for abutting tissue to be stitched positioned at the attachment point of the base structure to the aperture means.

5. The suture of claim 1 further including a needle associated with the needle end.

6. The suture of claim 1 wherein a hinged flap is positioned within said collar for allowing unidirectional movement of base structure and associated node therethrough.

7. A ligature comprising:
   an elongate surface having a longitudinal axis with a free end and a second end;
   evenly spaced lateral ribs traversing said elongate surface, said ribs each having an edge, proximal the free end and distal the second end, at least partially perpendicular to the longitudinal axis of the elongate surface;
   a notch, planar in longitudinal cross-section, positioned on the elongate surface between said ribs, the longitudinal plane of said notch laying substantially parallel to the elongate surface's longitudinal axis; and
   means, associated with the second end of the ligature, for unidirectionally impeding movement of the ligature through said means, while allowing movement in a direction opposite to the impeded direction, said means further having an aperture sized to allow limited bi-directional movement of said means over said notch between two of said evenly spaced lateral ribs, said ribs having a convex top surface to facilitate entry and placement of the ribs in the aperture.

* * * * *